US012590956B2

(12) United States Patent　(10) Patent No.: US 12,590,956 B2
Farmer　(45) Date of Patent:　Mar. 31, 2026

(54) LATERAL FLOW TEST APPARATUS

(71) Applicant: Owen Mumford Limited, Woodstock (GB)

(72) Inventor: Matthew David Farmer, Woodstock (GB)

(73) Assignee: OWEN MUMFORD LIMITED, Woodstock (GB)

( * ) Notice: Subject to any disclaimer, the term of this patent is extended or adjusted under 35 U.S.C. 154(b) by 344 days.

(21) Appl. No.: 17/679,271

(22) Filed: Feb. 24, 2022

(65) Prior Publication Data

US 2022/0308051 A1　Sep. 29, 2022

(30) Foreign Application Priority Data

Mar. 29, 2021　(GB) ...................................... 2104453

(51) Int. Cl.
　　*G01N 33/543*　(2006.01)
　　*B01L 3/00*　(2006.01)
(52) U.S. Cl.
　　CPC ...... *G01N 33/54388* (2021.08); *B01L 3/5023* (2013.01); *B01L 2300/069* (2013.01); *B01L 2400/0406* (2013.01)
(58) Field of Classification Search
　　CPC ..... B01L 2300/0825; B01L 2300/0838; G01N 33/54386–54391
　　See application file for complete search history.

(56) References Cited

U.S. PATENT DOCUMENTS

| | | | |
|---|---|---|---|
| 2011/0027908 A1* | 2/2011 | Siciliano | .......... G01N 33/56911 |
| | | | 422/69 |
| 2012/0301893 A1* | 11/2012 | Siciliano | ........... B01L 3/502738 |
| | | | 435/7.1 |
| 2014/0272941 A1* | 9/2014 | Gunnerson | ......... B01L 3/50273 |
| | | | 435/7.1 |
| 2019/0317115 A1 | 10/2019 | MacLean et al. | |
| 2020/0345286 A1 | 11/2020 | Collovati | |
| 2021/0178389 A1 | 6/2021 | Bullington et al. | |

FOREIGN PATENT DOCUMENTS

| | | | | |
|---|---|---|---|---|
| WO | WO-2018128749 A1 * | 7/2018 | ............ | B01L 3/5023 |
| WO | 2020260250 A1 | 12/2020 | | |

OTHER PUBLICATIONS

Search Report, related UK Application No. GB2104453.2, mailed Aug. 6, 2021, 1 page.

* cited by examiner

*Primary Examiner* — Maris R Kessel
*Assistant Examiner* — Alea N. Martin
(74) *Attorney, Agent, or Firm* — QUARLES & BRADY LLP

(57) ABSTRACT

A lateral flow test apparatus comprising a housing and a test strip located within the housing. The apparatus further comprises a capillary tube having first and second ends, the first end configured to receive a fluid sample to be tested, and the second opposed end, the housing and the test strip defining an air gap between said second end and a fluid sample receiving region of said test strip, and a user actuable mechanism configured to move said receiving region across said air gap and into contact with said second end, whereby, in use, a sample fluid within said capillary tube is drawn from the capillary tube into said receiving region.

10 Claims, 7 Drawing Sheets

LATERAL FLOW TEST APPARATUS

CROSS-REFERENCE TO RELATED APPLICATIONS

This application claims priority to and the benefit of British Patent Application Serial No. GB2104453.2, filed Mar. 29, 2021, and entitled, "LATERAL FLOW TEST APPARATUS," the entire contents of which are incorporated by reference herein.

TECHNICAL FIELD

The present invention relates to lateral flow test apparatus and in particular, though not necessarily, so such apparatus that are used to test a biological sample such as a human biological sample.

BACKGROUND

Lateral flow test apparatus or devices are typically relatively simple devices intended to detect the presence of a target substance in a liquid sample without the need for specialized and costly equipment. These tests are widely used in medical diagnostics for home testing, point of care testing, or laboratory use. For instance, the home pregnancy test is a lateral flow test that detects a certain hormone. These tests are simple, economic and generally show results in around five to 30 minutes. Lateral flow tests devices have also been hugely important in the response to the ongoing Covid-19 pandemic. Biological samples commonly tested by lateral flow test devices include blood, saliva, and sputum.

In many lateral flow test devices, the amount of sample fluid applied to the test strip can be critical. Either too much fluid or too little fluid can give rise to an erroneous result. This can be problematic where a capillary tube or passage is fixed to the device and is used to draw the sample fluid from a source, such as a blood droplet on a user's finger, onto an end of the test strip (typically provided with an absorbent pad). It is in this case extremely difficult to have the user withdraw his or her finger at the point where the volume of fluid drawn is just right. To address this problem it is known to use a detached capillary tube which is first applied to the source of sample fluid until filled, and then moved into contact with the pad of the test strip. This however requires the tube to be provided as a separate component or at least as a component that is movable relative to the rest of the device.

SUMMARY

According to a first aspect of the present invention there is provided a lateral flow test apparatus comprising a housing and a test strip located within the housing. The apparatus further comprises a capillary tube having first and second ends, the first end configured to receive a fluid sample to be tested, and the second opposed end, the housing and the test strip defining an air gap between said second end and a fluid sample receiving region of said test strip, and a user actuable mechanism configured to move said receiving region across said air gap and into contact with said second end, whereby, in use, a sample fluid within said capillary tube is drawn from the capillary tube into said receiving region.

The capillary tube may be molded integrally with said housing or with a housing part making up the housing. The capillary tube may have an opening running along the whole or a part of the tube. The second end of the capillary tube may open into an enlarged opening defined by the housing or a housing part.

The test strip may comprise a porous wicking strip and a porous sample pad in contact with the porous wicking strip, said sample receiving region being a region of said porous sample pad.

The user actuable mechanism may comprise a button extending through said housing or a housing part and moveable between a first pre-use state and a second activated state, whereby movement of the button from the first to the second state causes movement of said receiving region across said air gap and into contact with said second end.

The button and housing may define two snap fit positions providing said first and second states.

The housing may comprise upper and lower housing parts between which said test strip is located.

The user actuable mechanism may comprise a button, slider or lever coupled to a ramp or other means providing a cam surface.

According to a second aspect of the present invention there is provided a lateral flow test apparatus comprising a housing configured to receive a test strip. The apparatus further comprises a capillary tube having first and second ends, the first end configured to receive a fluid sample to be tested, and the second opposed end, the housing and the test strip, when installed, defining an air gap between said second end and a fluid sample receiving region of said test strip, and a user actuable mechanism configured to move said receiving region across said air gap and into contact with said second end, whereby, in use, a sample fluid within said capillary tube is drawn from the capillary tube into said receiving region.

DETAILED DESCRIPTION

As has been noted above, lateral flow test apparatus or devices provide a very simple and relatively cheap way of performing various tests on a sample of biological fluid ("sample"). It is desirable however to integrate into the devices a means to control, relatively precisely, the volume of sample offered up to the test strip. Any such means should be as simple as possible.

Figure 1C:
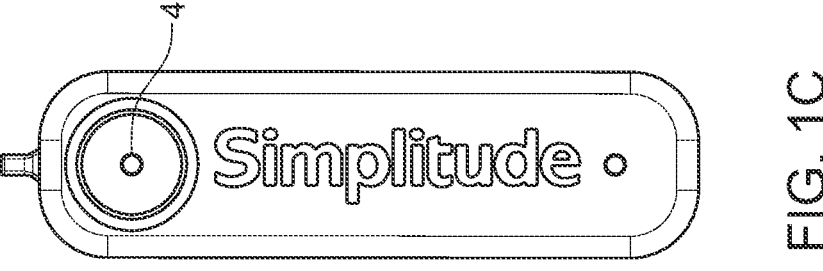
FIG. 1 shows a lateral flow test device in panel (a) upper plan view, panel (b) side view, and panel (c) lower plan view.
Figure 1B:
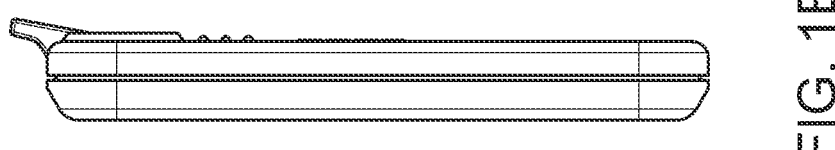
Figure 1A:
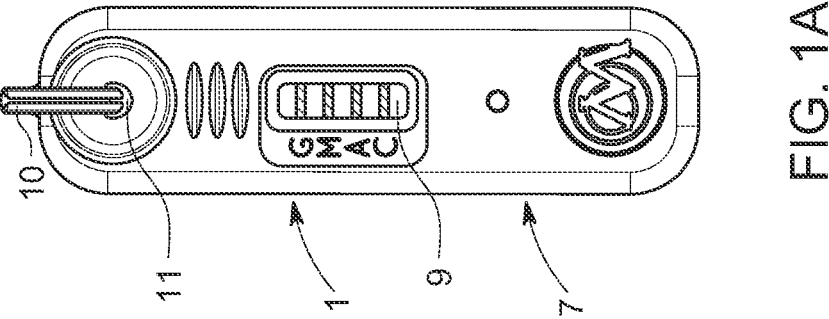
Figure 2:
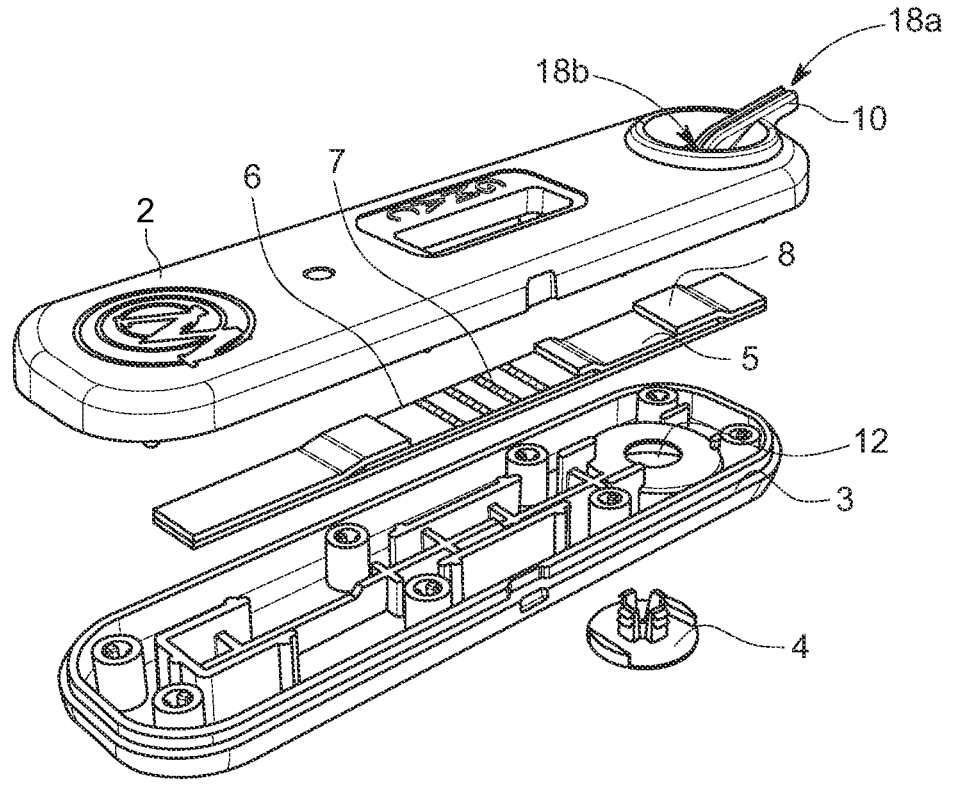
FIG. 2 is an exploded perspective view of the device of FIG. 1.

FIG. 1 illustrates an exemplary lateral flow test device 1, where view (a) is a top plan view of the device, (b) is a side view, and (c) is a bottom plan view. The device 1 is extremely simple in its construction as is best shown in the exploded perspective view of FIG. 2. The device comprises three principle injection molded plastic components including: an upper housing part 2 and a lower housing part 3 which together define a device housing 17, and a transfer button 4. A lateral flow test strip 5 is sandwiched between the upper and lower housing parts such that it is gripped by features of these parts when the parts are secured together, e.g. via a snap-fit arrangement. The lateral flow test strip 5 will not be described here in detail as it may be of known construction. It is sufficient to note that it comprises a porous wicking strip 6 on which are located indicator "lines" 7 of reactive molecules (four such lines are shown in the Figures) configured to perform the test or tests of interest, and a porous sample pad 8 located at one end of the strip.

The upper housing part 2 defines a substantially rectangular opening or window 9 through which the indicator lines 7 are visible. Markers are provided on the upper housing part, adjacent the window, to identify the lines (in this case "G", "M", "A" and "C"). The upper housing part further defines a capillary tube 10 that is open along its upper surface and at both ends, 18a, 18b. The tube, which may be molded integrally with the upper housing part, opens at one end into a generally circular flow through opening 11 formed in the upper housing part. The device is configured such that the opening 11 is located directly above the sample pad 8. It will be noted that the flow through opening 11 extends around the end 18b of the capillary tube such that a space beneath the tube, within the housing, is visible.

The transfer button 4 is located within a generally circular lower opening 12 formed in the lower housing part 3. As will be clear from the following discussion concerning FIGS. 3(a) to (d), the button comprises a button head 13 at its lower end and, extending upwardly therefrom, a generally cylindrical split pin 14. A pair of circular barbs 15a,b extend around the outer surface of the split pin. During assembly, the button is engaged with the lower housing part by pressing the button into the lower opening 12 such that the uppermost barb 15a engages with the periphery of the lower opening. The axial spacing between the upper and lower barbs is such that, in this configuration, the button is securely retained within the lower opening. Furthermore, in this pre-use configuration, the test strip substantially rests on the upper end of the button such that the upper surface 16 of the sample pad 8 is spaced apart from the lowermost surface of the flow through opening 11. NB. The test strip 5 is clamped (to at least some extent) at both ends between the two housing parts such that the upper surface 16 of the sample pad 8 does not move to any significant extend in its pre-use state.

Figure 3A:
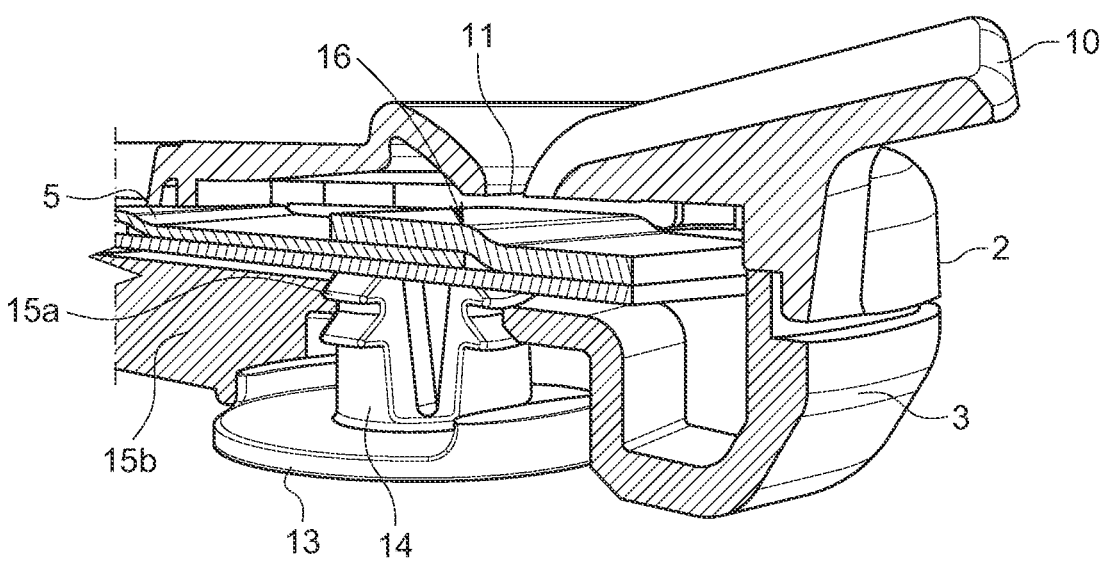
FIG. 3 panels (a) to (d) illustrate steps in performing a test using the device of FIGS. 1 and 2.
Figure 3B:
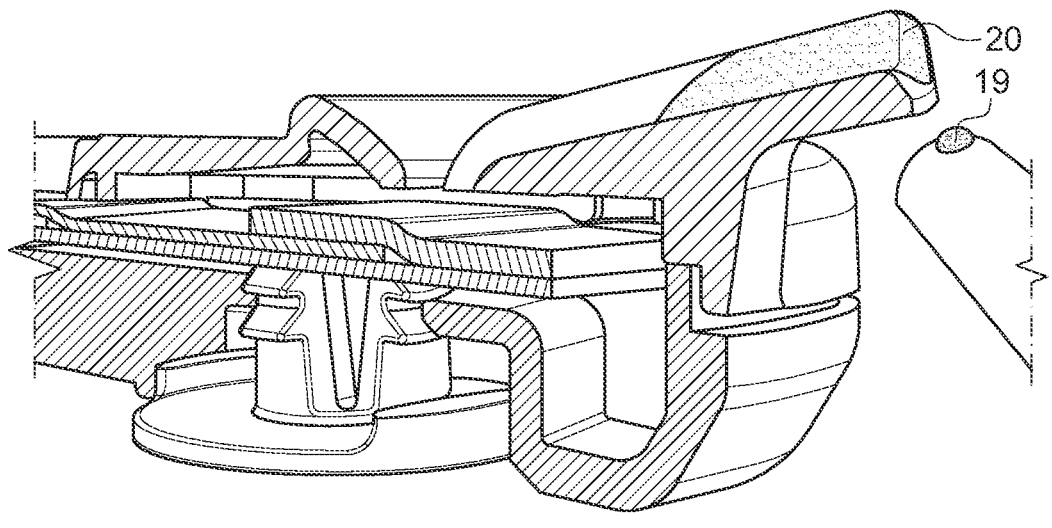
Figure 3C:
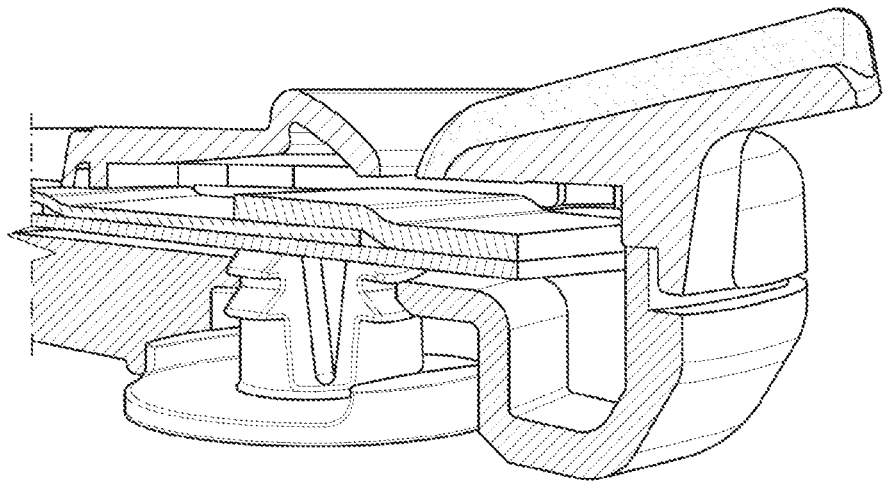

Use of the device 1 will now be described with reference to the cross-sectional views of FIGS. 3(a) to (d), which show a detail of the end of the device at which the capillary tube 10 and button 4 are provided, where FIG. 3(a) shows a pre-use state. To perform a test (assuming that the sample is a blood sample), a user first pricks his or her finger with a needle or lancet. Such a needle or lancet may be provided as a separate component or may be integrated into the device. This will cause a spot of blood to form on the skin. The user brings the droplet 19 into contact with the exposed end of the capillary tube 10 as shown in FIG. 3(b), causing blood 20 to be drawn from the drop into the tube. Blood is drawn into the tube until the tube is completely filled, as shown in FIG. 3(c). Blood does not flow out of the lower end of the tube as that end is exposed only to air. The user then withdraws his or her finger leaving a precisely defined volume of blood in the tube. It will be noted that the opening along the upper surface of the capillary tube 10 provides a visual indication to the user that the tube is being filled. This could otherwise be achieved by making the tube of a transparent material.

Figure 3D:
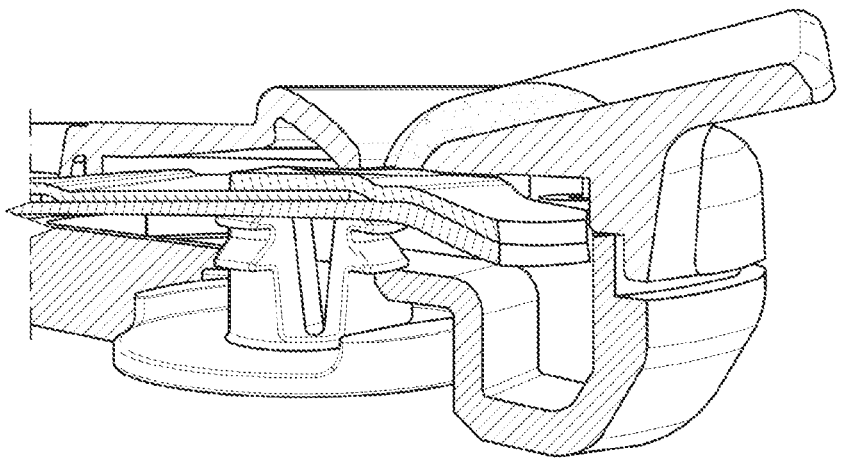
Figure 4C:
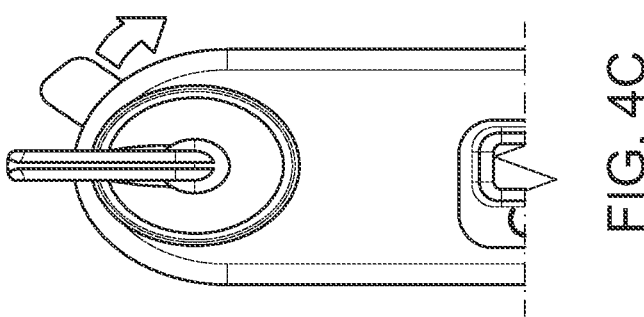
FIG. 4 panels (a) to (g) illustrate exemplary lateral flow test devices.
Figure 4B:
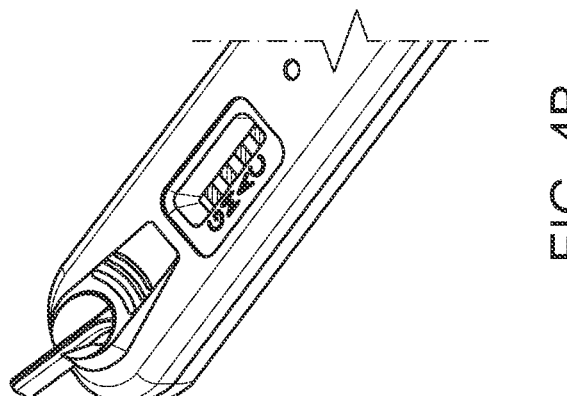
Figure 4A:
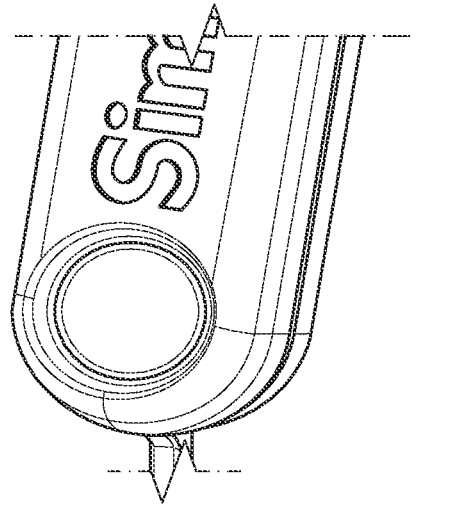
Figure 4F:
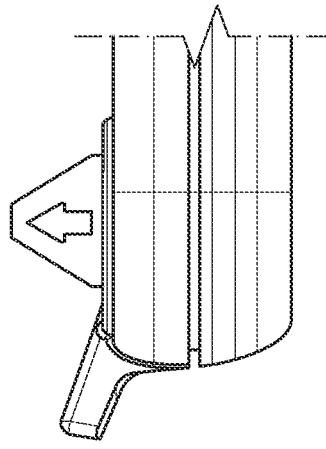
Figure 4E:
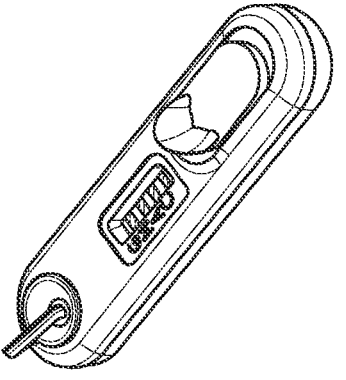
Figure 4D:
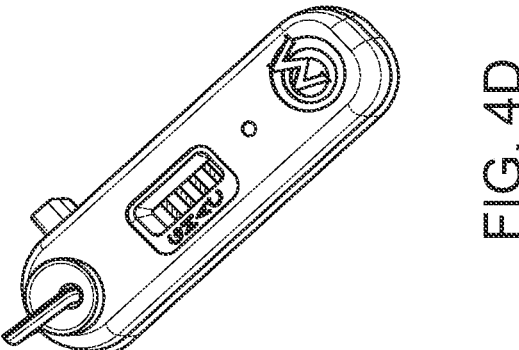
Figure 4G:
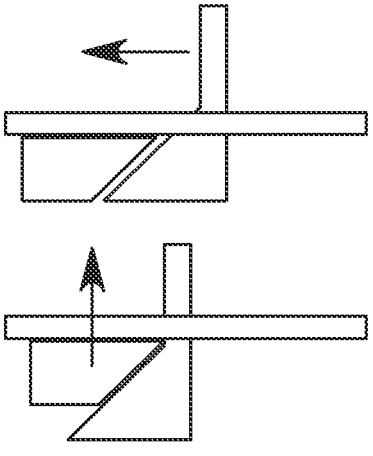

The next step in the procedure is for the user to fully depress the button 4 into the lower housing part 2. This causes the lowermost barb 15b to snap into the lower opening 12. Again, the dimensions of the button and opening, including the thickness of the lower housing part, are such that the button is retained in the depressed position with little or no freedom to move. As can be seen in FIG. 3(d), fully depressing the button 4 forces the end of the test strip 5, including the sample pad 8, to move upwards, bringing the pad into contact with the periphery of the flow through opening 11 and with the blood at the lower end of the capillary tube 10. At this stage, blood is absorbed into the pad from the capillary tube until the tube is substantially emptied. It will be appreciated that, assuming that the pad 8 is of a light or otherwise contrasting colour, the user will observe a visible red spot form on the pad through the opening. This gives visual feedback to the user that the button has been pressed and the test is in progress.

The presented sample may then flow along the porous wicking strip 6 with appropriate, visible, reactions occurring at the lines 7. A buffer or other transport fluid may need to be inserted through the flow through opening 11, e.g. by squeezing drops out of a bottle or vial, to cause the sample to be moved along the strip 6. In some cases, a vial of transport fluid may be integrated into the device with means for releasing the fluid above or otherwise into the pad 8.

FIGS. 3(a) to (g) illustrate various exemplary embodiments of a lateral flow test device as follows:

(a) Use of a button provided in the lower housing part as described above with reference to FIGS. 1 and 2.

(b) Use of a lever mounted with the upper housing part, such that movement of the lever from a first to a second position presses the end of the capillary tube downwards onto the sample pad.

(c) A side lever is mounted within the lower housing part. This might present a cam surface against the underside of the test strip which presses the strip and pad upwards as the lever is moved.

(d) A button is mounted within the lower housing part and presents a ramp to the underside of the test strip.

(e) A slider is provided in the upper housing part at an end opposed to the flow through opening. Movement of the slider causes a ramp to move under the tests strip and push it upwards.

It will be appreciated by the skilled person that various modifications may be made to the above described embodiments without departing from the scope of the present invention. For example, whilst the capillary tubed is described above as being open along its upper extent, the tube may alternatively be closed.

The invention claimed is:

1. A lateral flow test apparatus comprising a housing and an elongated test strip located within the housing, the apparatus further comprising:

a capillary tube having first and second ends, the first end configured to receive a fluid sample to be tested, the second opposed end, the housing, and the test strip defining an air gap between said second end and the fluid sample receiving region of said test strip, and the second opposed end being configured to be located adjacent to a fluid sample receiving region of said test strip; and a user actuatable mechanism comprising a button configured to move said receiving region across said air gap and into contact with said second end, whereby, in use, a sample fluid within said capillary tube is drawn from the capillary tube into said receiving region, wherein the user actuatable mechanism is configured to be adjacent to the elongated test strip, wherein the elongated test strip comprises a long axis, wherein the user actuatable mechanism moves said receiving region in a perpendicular direction relative to the long axis toward the second end of the capillary tube, and wherein the button comprises a first barb and a second barb and wherein, prior to depression of the button, the first barb is configured to engage with the housing in a first snap-fit configuration and wherein, upon depression of the button by a user, the second barb is configured to engage with the housing in a second snap-fit configuration.

2. Apparatus according to claim 1, wherein said capillary tube is molded integrally with said housing or with a housing part making up the housing.

3. Apparatus according to claim 1, wherein said capillary tube has an opening running along the whole or a part of the tube.

4. Apparatus according to claim 1, wherein said second end of the capillary tube opens into an enlarged opening defined by the housing or a housing part.

5. Apparatus according to claim 1, wherein said test strip comprises a porous wicking strip and a porous sample pad in contact with the porous wicking strip, said sample receiving region being a region of said porous sample pad.

6. Apparatus according to claim 1, wherein said user actuatable mechanism comprising the button extends through said housing or a housing part and is moveable between a first pre-use state and a second activated state, whereby movement of the button from the first to the second state causes movement of said receiving region across said air gap and into contact with said second end.

7. Apparatus according to claim 6, wherein said button and housing define two snap fit positions providing said first and second states.

8. Apparatus according to claim 1, wherein said housing comprises upper and lower housing parts between which said test strip is located.

9. Apparatus according to claim 1, wherein said user actuatable mechanism is coupled to a ramp or other means providing a cam surface.

10. A lateral flow test apparatus comprising a housing configured to receive an elongated test strip, the apparatus further comprising:

a capillary tube having first and second ends, the first end configured to receive a fluid sample to be tested, the second opposed end, the housing, and the test strip, when installed, defining an air gap between said second end and a fluid sample receiving region of said test strip, and the second opposed end being configured to be located adjacent to a fluid sample receiving region of said test strip; and a user actuatable mechanism comprising a button configured to move said receiving region across said air gap and into contact with said second end, whereby, in use, a sample fluid within said capillary tube is drawn from the capillary tube into said receiving region, wherein the user actuatable mechanism is configured to be adjacent to the elongated test strip, wherein the elongated test strip comprises a long axis, wherein the user actuatable mechanism moves said receiving region in a perpendicular direction relative to the long axis toward the second end of the capillary tube, and wherein the button comprises a first barb and a second barb and wherein, prior to depression of the button, the first barb is configured to engage with the housing in a first snap-fit configuration and wherein, upon depression of said button by a user, the second barb is configured to engage with the housing in a second snap-fit configuration.

* * * * *